United States Patent
Schader et al.

(10) Patent No.: US 11,419,992 B2
(45) Date of Patent: Aug. 23, 2022

(54) MEDICAMENT INJECTION DEVICE

(71) Applicant: Sanofi-Aventis Deutschland GmbH, Frankfurt am Main (DE)

(72) Inventors: Marc Schader, Frankfurt am Main (DE); Michael Helmer, Frankfurt am Main (DE); Sebastian Braun, Darmstadt (DE); Michael Varga, Donzdorf (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 1088 days.

(21) Appl. No.: 15/778,794

(22) PCT Filed: Nov. 21, 2016

(86) PCT No.: PCT/EP2016/078266
§ 371 (c)(1),
(2) Date: May 24, 2018

(87) PCT Pub. No.: WO2017/089277
PCT Pub. Date: Jun. 1, 2017

(65) Prior Publication Data
US 2018/0353709 A1 Dec. 13, 2018

(30) Foreign Application Priority Data
Nov. 27, 2015 (EP) .................................... 15196698

(51) Int. Cl.
*A61M 5/32* (2006.01)
*A61M 5/20* (2006.01)
(Continued)

(52) U.S. Cl.
CPC .......... *A61M 5/3245* (2013.01); *A61M 5/178* (2013.01); *A61M 5/20* (2013.01);
(Continued)

(58) Field of Classification Search
CPC .............. A61M 5/3245; A61M 5/2466; A61M 5/2455; A61M 2005/2474;
(Continued)

(56) References Cited

U.S. PATENT DOCUMENTS 4,936,830 A * 6/1990 Verlier .................. A61M 5/283
604/110
2003/0144633 A1 7/2003 Kirchhofer
(Continued)

FOREIGN PATENT DOCUMENTS

| CN | 1030529 | 1/1989 |
|---|---|---|
| CN | 102844065 | 12/2012 |

(Continued)

OTHER PUBLICATIONS

International Search Report and Written Opinion in International Application No. PCT/EP2016/078266 , dated Jan. 9, 2017, 8 pages.
(Continued)

*Primary Examiner* — Nilay J Shah
(74) *Attorney, Agent, or Firm* — Fish & Richardson P.C.

(57) ABSTRACT

A medicament injection device comprising: a main body configured to receive a medicament cartridge, a needle sleeve axially movable with respect to the main body, a needle holder holding a needle, and a displacement element coupled to the needle holder and disengageably coupled to the needle sleeve; wherein, upon axial displacement of the needle sleeve by a predefined distance in a proximal direction, the needle carrier and needle are displaced axially in a proximal direction.

20 Claims, 4 Drawing Sheets

(51) Int. Cl.
*A61M 5/178* (2006.01)
*A61M 5/28* (2006.01)
*A61M 5/315* (2006.01)
*A61M 5/24* (2006.01)

(52) U.S. Cl.
CPC ........ *A61M 5/285* (2013.01); *A61M 5/31543* (2013.01); *A61M 5/31546* (2013.01); *A61M 5/3234* (2013.01); *A61M 2005/2474* (2013.01); *A61M 2005/3254* (2013.01); *A61M 2005/3267* (2013.01)

(58) Field of Classification Search
CPC ............ A61M 2005/247; A61M 5/285; A61M 2005/3267; A61M 5/178; A61M 5/20; A61M 5/3271; A61M 5/3234; A61M 2005/3254; A61M 5/326; A61M 5/32; A61M 5/3293; A61M 5/344; A61M 5/346; A61M 5/348; A61M 2005/2013; A61M 2005/206; A61M 2005/208; A61M 5/3202; A61M 5/321; A61M 5/3219; A61M 5/322; A61M 5/3221; A61M 5/3232; A61M 2005/3235; A61M 2005/3236; A61M 2005/3238; A61M 5/31586
See application file for complete search history.

(56) References Cited

U.S. PATENT DOCUMENTS

| | | | |
|---|---|---|---|
| 2007/0100290 A1 | 5/2007 | Schiffmann et al. | |
| 2012/0277685 A1 | 11/2012 | Limaye | |
| 2012/0283616 A1 | 11/2012 | Edme et al. | |
| 2012/0283646 A1 | 11/2012 | Kouyoumjian et al. | |
| 2013/0211330 A1* | 8/2013 | Pedersen | A61M 5/2033 604/111 |
| 2014/0243741 A1* | 8/2014 | Kaufmann | A61M 5/2066 604/88 |
| 2014/0243755 A1* | 8/2014 | Slemmen | A61M 5/3257 604/198 |
| 2015/0119815 A1 | 4/2015 | Fuke et al. | |
| 2015/0190580 A1 | 7/2015 | Imai et al. | |

FOREIGN PATENT DOCUMENTS

| | | | |
|---|---|---|---|
| CN | 104470562 | 3/2015 | |
| CN | 104768598 | 7/2015 | |
| EP | 2875838 | 5/2015 | |
| GB | 2206800 | 1/1989 | |
| JP | H06-052837 U | 7/1994 | |
| JP | 2007-075610 | 3/2007 | |
| JP | 2012-232136 | 11/2012 | |
| WO | WO 2011/095486 | 8/2011 | |
| WO | WO 2014/013594 | 1/2014 | |
| WO | WO-2014001318 A2 * | 1/2014 | ........ A61M 5/31583 |
| WO | WO-2014001319 A1 * | 1/2014 | .......... A61M 5/3257 |
| WO | WO 2014/064100 | 5/2014 | |
| WO | WO 2014/112426 | 7/2014 | |

OTHER PUBLICATIONS

International Preliminary Report on Patentability in International Application No. PCT/EP2016/078266, dated May 29, 2018, 6 pages.

* cited by examiner

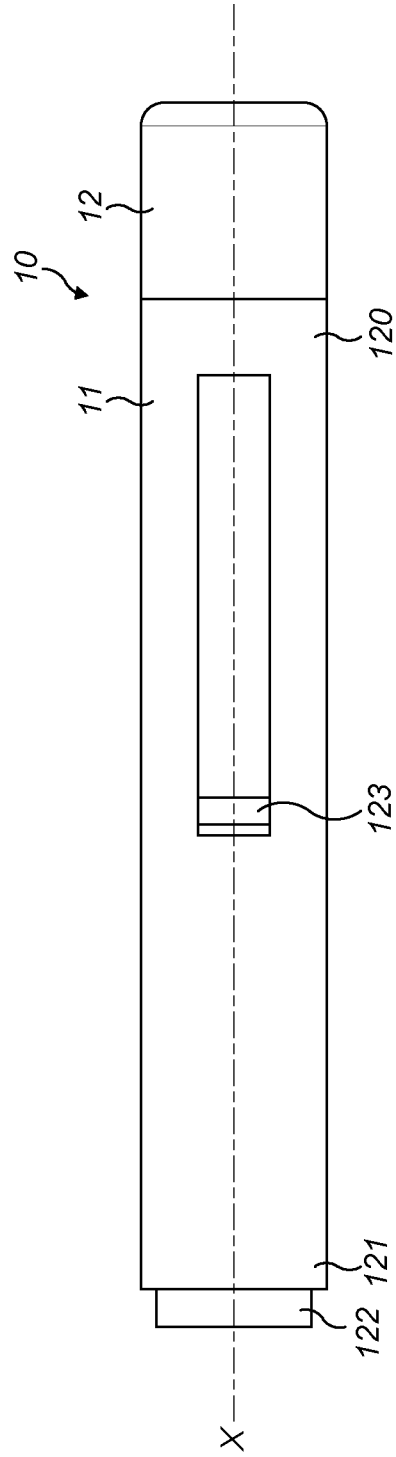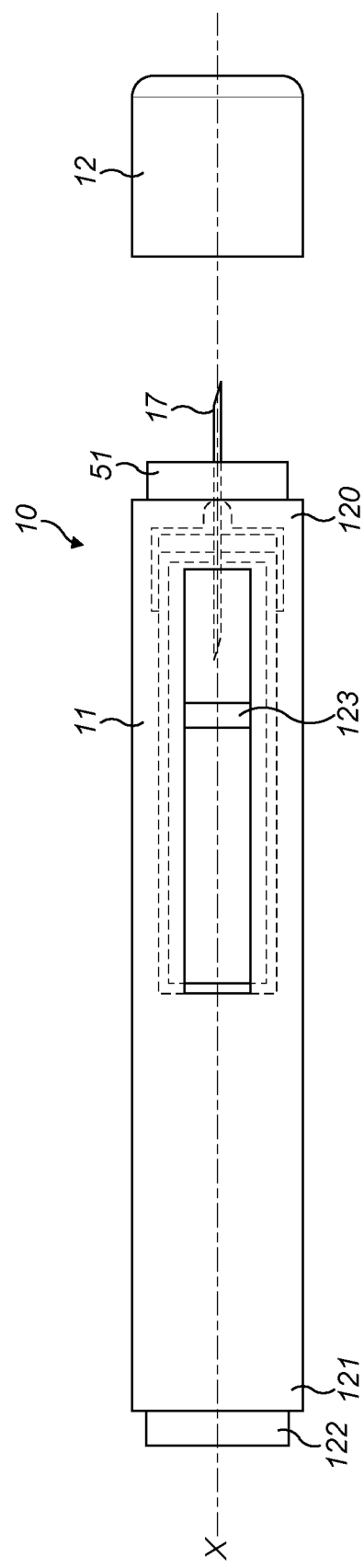

MEDICAMENT INJECTION DEVICE

CROSS REFERENCE TO RELATED APPLICATIONS

This application is a U.S. national stage application under 35 USC § 371 of International Patent Application No. PCT/EP2016/078266, filed on Nov. 21, 2016, which claims priority to European Patent Application No. 15196698.3, filed on Nov. 27, 2015, the entire contents of each of which are incorporated herein by reference.

TECHNICAL FIELD

The disclosure generally relates to a medicament delivery device.

BACKGROUND

Medicament injection devices can take the form of a syringe, whereby medicament is provided in a tubular barrel having a plunger and an outlet to which a needle is connected. A user connects the needle to the reservoir manually before the injection takes place. The attachment of the needle to the syringe requires some dexterity and is difficult for those having poor coordination, such as patients who have lost a degree of sensation in their hands.

While it is possible to provide injection devices in which the needle is pre-attached to a medicament cartridge, in certain situations it is desirable to provide a device in which the needle is kept separate from the medicament until such time as the user wishes to commence the injection.

SUMMARY

According to a first embodiment, there is provided a medicament injection device comprising: a main body configured to receive a medicament cartridge, a needle sleeve axially movable with respect to the main body, a needle holder holding a needle, and a displacement element coupled to the needle holder and disengageably coupled to the needle sleeve; wherein, upon axial displacement of the needle sleeve by a predefined distance in a proximal direction, the needle carrier and needle are displaced axially in a proximal direction.

Further axial movement in the proximal direction of the needle sleeve beyond the predefined distance may cause disengagement of the needle sleeve from the displacement element.

The displacement element may comprise at least one ramped surface.

The displacement element may comprise at least one slot.

The needle sleeve may comprise at least one pin arranged to slide through the slot when the displacement element and the needle sleeve are in rotational alignment.

The further axial movement of the needle sleeve may cause a rotational movement of the pin with respect to the ramped surface so that the pin aligns with the slot, thereby causing the disengagement of the needle sleeve from the displacement element.

The needle sleeve may have two pins located circumferentially opposite from each other on an inner circumferential wall of the needle sleeve and the displacement element has two respective slots for receiving the two pins located circumferentially opposite from each other.

The device may contain a medicament cartridge, wherein the axial displacement of the needle carrier and needle in a proximal direction causes the proximal end of the needle to pierce a cartridge septum.

The medicament cartridge may comprise a male part and the needle holder may comprise a female part and wherein the male part and female part are configured to form a frictional fit subsequent to displacement of the needle holder by the predefined distance.

The needle holder may further comprise a lip to prevent subsequent axial displacement of the needle carrier and needle with respect to the medicament cartridge subsequent to axial displacement of the displacement part by the predefined distance.

The device may contain a medicament cartridge containing a medicament.

According to a second embodiment, there is provided a method of operating a medicament injection device, the method comprising: pushing a needle sleeve disengageably coupled to a displacement element in a proximal axial direction thereby causing proximal movement of a needle carrier and needle, wherein a proximal end of the needle is caused to pierce a penetrable barrier of a medicament cartridge.

Further proximal axial displacement of the needle sleeve may cause an uncoupling of the needle sleeve from the displacement element.

BRIEF DESCRIPTION OF THE DRAWINGS

So that the disclosure can be fully understood, embodiments thereof will be described with reference to the accompanying drawings, in which:

FIGS. 1A and 1B are side-on views of an auto-injector device according to an embodiment;

DETAILED DESCRIPTION

Figure 2:
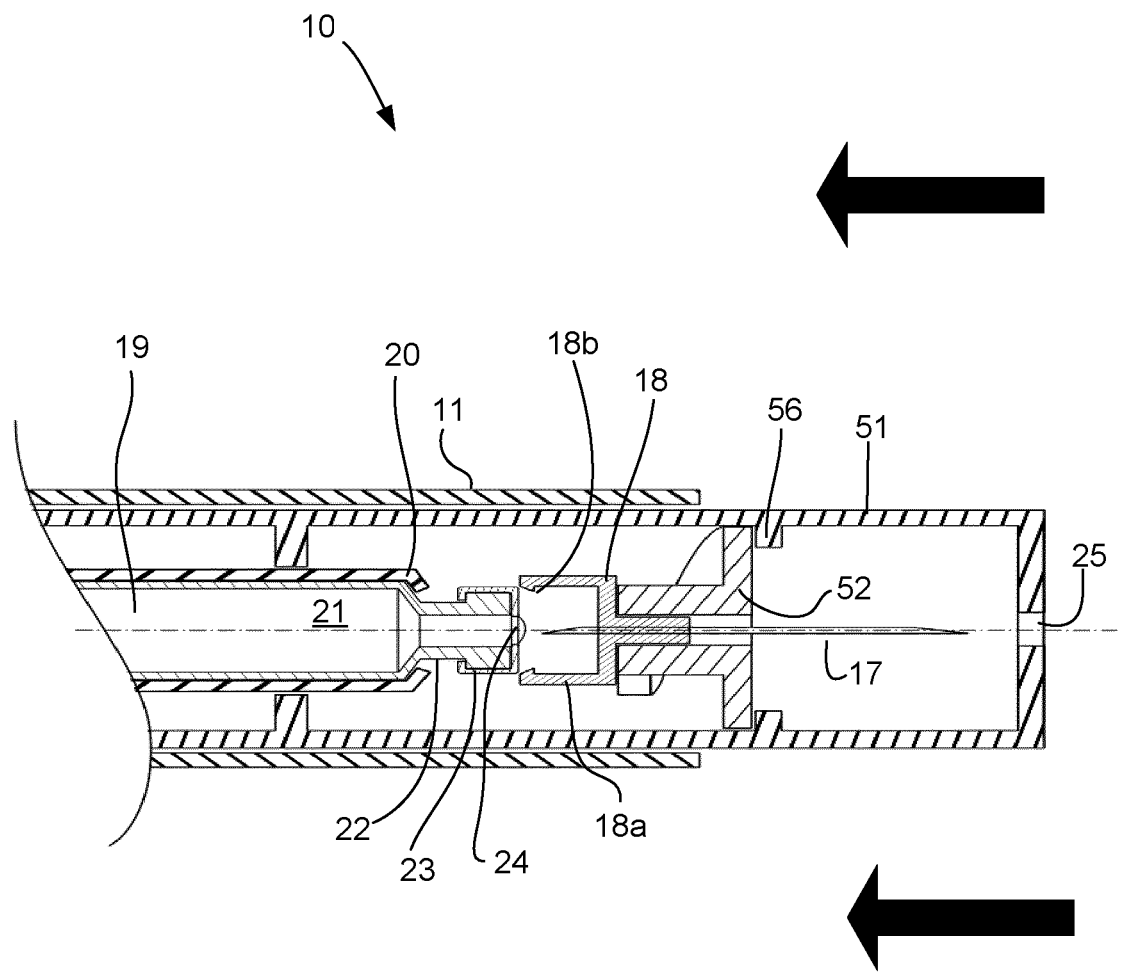
FIG. 2 is a side-on cross sectional schematic view of the device shown in FIG. 1.

Some embodiments provide a mechanism for inserting the needle of an injection device such as an auto-injector or syringe into a medicament cartridge containing the medicament to be injected. Providing such a mechanism allows the medicament cartridge to be sealed until such time as the user wishes to commence the injection. Providing an automated mechanism for inserting the needle into the medicament cartridge also reduces the amount of handling of the needle by the user prior to the injection. Indeed, in some embodiments the user does not need to touch the needle during the steps of inserting the needle into the medicament cartridge and subsequently actuating the injection of the medicament.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a main body 11 which typically contains a reservoir containing the medicament to be injected (e.g., a syringe) and the components required to facilitate one or more steps of the delivery process. Device 10 can also include a cap assembly 12 that can be detachably mounted to the main body 11. Typically, a user must remove cap 12 from housing 11 before device 10 can be operated.

As shown, main body 11 is substantially cylindrical and has a substantially constant diameter along the longitudinal axis X. The housing 11 has a distal region 120 and a proximal region 121. The term "distal" refers to a location that is relatively closer to a site of injection, and the term "proximal" refers to a location that is relatively further away from the injection site.

Device 10 can also include a needle sleeve 51 coupled to main body 11 to permit movement of sleeve 51 relative to main body 11. For example, sleeve 51 can move in a longitudinal direction parallel to longitudinal axis X. Specifically, movement of sleeve 51 in a proximal direction can permit a needle 17 to extend from distal region 120 of main body 11.

Insertion of needle 17 can occur via several mechanisms. For example, needle 17 may be fixedly located relative to housing 11 and initially be located within an extended needle sleeve 51. Proximal movement of sleeve 51 by placing a distal end of sleeve 51 against a patient's body and moving main body 11 in a distal direction will uncover the distal end of needle 17. Such relative movement allows the distal end of needle 17 to extend into the patient's body. Such insertion is termed "manual" insertion as needle 17 is manually inserted via the patient's manual movement of main body 11 relative to sleeve 51.

Another form of insertion is "automated," whereby needle 17 moves relative to main body 11. Such insertion can be triggered by movement of sleeve 51 or by another form of activation, such as, for example, a button 122. As shown in FIGS. 1A & 1B, button 122 is located at a proximal end of main body 11. However, in other embodiments, button 122 could be located on a side of main body 11.

Other manual or automated features can include drug injection or needle retraction, or both. Injection is the process by which a bung or piston 123 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 121 of main body 11, and a distal end of the drive spring can be configured to apply a compressive force to a proximal surface of piston 123. Following activation, at least part of the energy stored in the drive spring can be applied to the proximal surface of piston 123. This compressive force can act on piston 123 to move it in a distal direction. Such distal movement acts to compress the liquid medicament within the syringe, forcing it out of needle 17.

Following injection, needle 17 can be retracted within sleeve 51 or main body 11. Retraction can occur when sleeve 51 moves distally as a user removes device 10 from a patient's body. This can occur as needle 17 remains fixedly located relative to main body 11. Once a distal end of sleeve 51 has moved past a distal end of needle 17, and needle 17 is covered, sleeve 51 can be locked. Such locking can include locking any proximal movement of sleeve 13 relative to main body 11.

Another form of needle retraction can occur if needle 17 is moved relative to main body 11. Such movement can occur if the syringe within main body 11 is moved in a proximal direction relative to main body 11. This proximal movement can be achieved by using a retraction spring (not shown), located in distal region 120. A compressed retraction spring, when activated, can supply sufficient force to the syringe to move it in a proximal direction. Following sufficient retraction, any relative movement between needle 17 and main body 11 can be locked with a locking mechanism. In addition, button 122 or other components of device 10 can be locked as required.

FIG. 2 shows a side-on cross-section of an auto-injector device 10 according to an embodiment.

The auto-injector device 10 comprises a cartridge 19 which is held in place by a cartridge holder 20. The cartridge holder 20 and cartridge 19 are connected and fixed relative to the main body 11 of the device 10. The cartridge 19 has a cartridge body 21 a neck 22 and a head 23. The head 23 is wider than the neck 22, thereby forming a flanged end. The neck 22 and head 23 contain a passage allowing medicament to pass therethrough as well as to receive the needle 17 once inserted. The head 23 is provided with a penetrable barrier such as a septum 24 to close off the passage and to seal the contents of the medicament cartridge 19. The cartridge body 21, neck 22 and head 23 may be generally cylindrical in shape. However, alternative shapes may be employed.

The needle holder 18 which holds the needle 17 is axially movable relative to the main body 11 and the cartridge 19. The needle holder has a generally cup-shaped portion 18a and a passage through which the needle 17 passes. The cup-shaped portion 18a is shaped to engage with the head 23 of the cartridge 19. The cup-shaped portion 18a comprises a lip 18b which serves to clip onto the head 23 to prevent detachment of the needle holder 18 from the cartridge 19 subsequent to attachment of the needle holder 18 to the cartridge 19.

The device 10 comprises a tubular needle sleeve 51. The needle sleeve 51 is a protective sleeve that prevents unwanted exposure of the needle 17. The needle sleeve has a generally similar shape to the main body and is hollow and generally cylindrical. The needle sleeve 51 fits inside the main body 11. The needle sleeve 51 is arranged so that it can slide axially relative to the main body 11. The needle sleeve 51 has an aperture 25 at the distal end thereof to allow the needle to contact the patient's skin.

The device shown in FIG. 2 shows the components of the device in their initial position prior to insertion of the needle into the medicament cartridge in preparation for the injection of medicament into the user.

Figure 3:
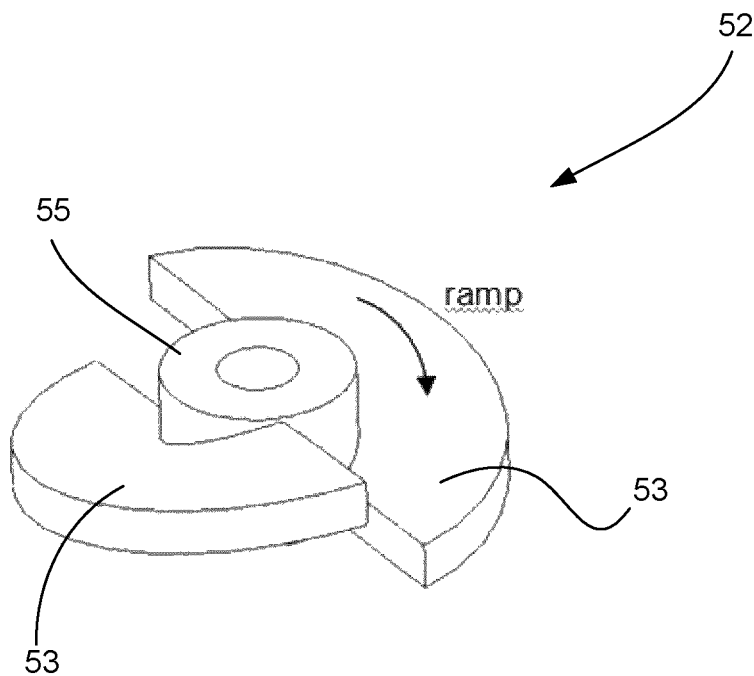
FIG. 3 is an elevated view of a displacement part.
Figure 4:
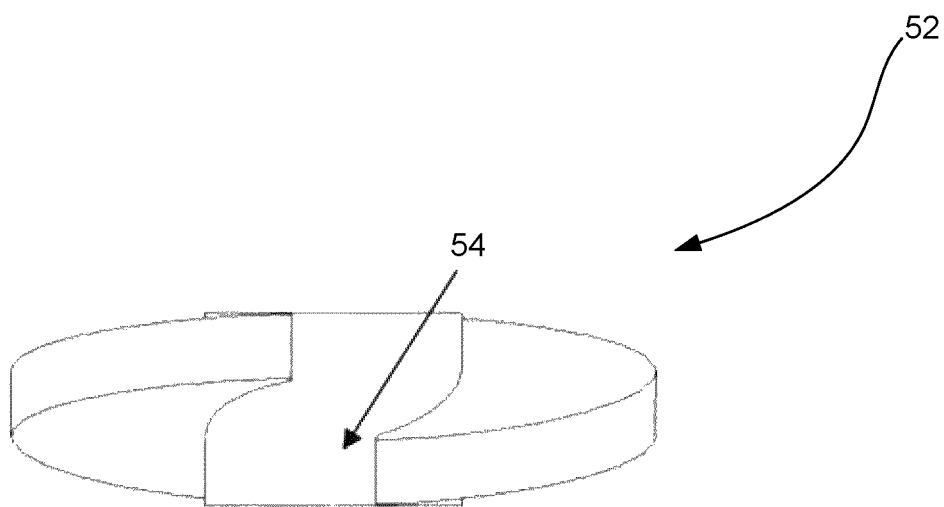
FIG. 4 is a side-on view of the displacement part shown in FIG. 3.

As shown in FIGS. 3 and 4, the needle holder displacement element 52 is generally circular in cross-section. The needle holder displacement element 52 comprises two ramped surfaces 53 (e.g., ramped semicircular surfaces) separated by grooves 54 arranged circumferentially opposite to each other. The central part of the needle holder displacement element 52 comprises a tubular portion 55 arranged to receive the needle 17 and needle holder 18 therein.

The interior surface of the wall of the needle sleeve 51 is provided with needle sleeve pins 56. In this embodiment, two pins 56 are provided, circumferentially opposite to each other. In use, the needle sleeve pins 56 push against the needle holder displacement element 52 when the needle sleeve 51 is pushed in the direction shown by the bold arrows in FIG. 2, i.e. towards the proximal end of the device 10. The engagement between the needle sleeve pins 56 and the ramped surfaces 53 of the needle holder displacement element 52 causes the needle holder displacement element 52 to move axially towards the medicament cartridge 19 as the needle sleeve 51 is moved. The needle holder displacement element 52 receives a distal portion of the needle holder 18 in the tubular portion 55 thereof. The axial movement of the needle holder displacement element 52 therefore causes the needle holder 18 and needle 17 to move axially towards the medicament cartridge 19.

Figure 5:
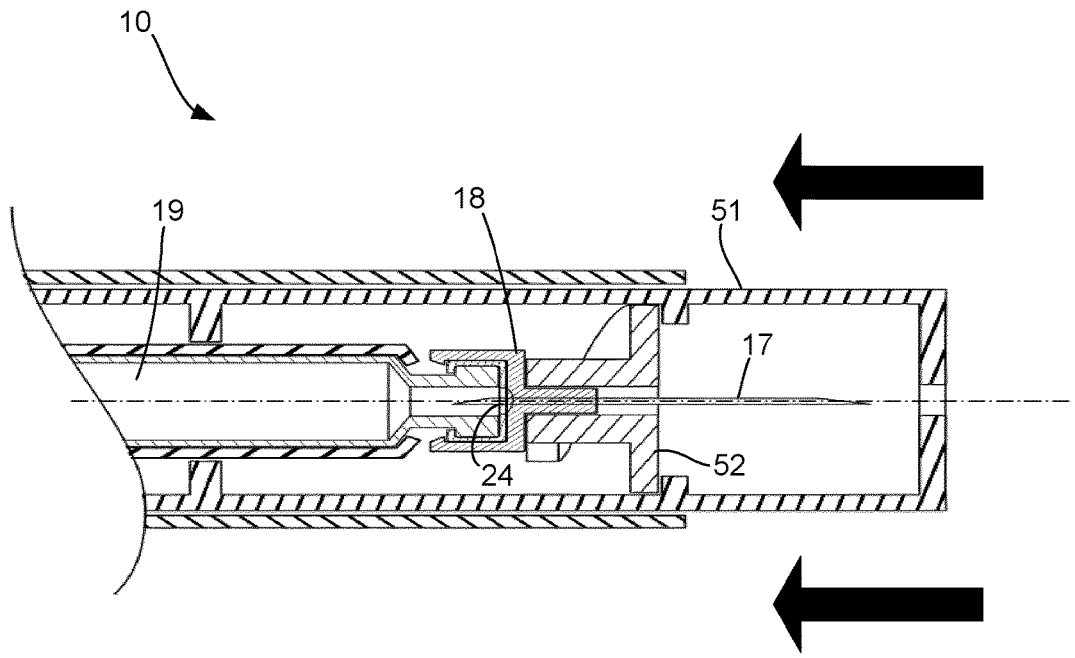
FIG. 5 is a side-on cross sectional schematic view of the device as the needle holder is attached to the medicament cartridge.

FIG. 5 shows a side-on cross-section of the auto-injector device 10 as the user pushes the needle sleeve 51 in the proximal direction as shown by the bold arrows. The needle sleeve 51 is coaxial with respect to main body and slides along inside the main body 11 of the device 10. After moving axially by a predefined distance, the cup-shaped part 18a of the needle holder 18 fits over the head 23 of the medicament cartridge 19. The diameter of the cup shaped part 18a and the diameter of the head 23 of the medicament cartridge 19 are arranged to ensure a close frictional fit between the needle holder 18 and the medicament cartridge 19. Moreover, the lip 18b extending around the cup-shaped part 18a of the needle holder further serves to fix the needle holder 18 to the medicament cartridge 19. The lip 18b has a tapered leading edge to allow the cup shaped part to fit over the head 23. However, once the needle holder 18 is fitted to the medicament cartridge 19, axial movement of the needle holder away (in a distal direction), and separation from, the medicament cartridge 19 is prevented by the lip and the frictional fit.

As shown in FIG. 5, the needle 17 pierces the septum 24 of the medicament cartridge 19, thereby establishing a passage for the medicament to flow from the medicament cartridge 19 to the distal end of the needle 17. Both ends of the needle 17 are sharp. The proximal end is sufficiently sharp to enable the needle 17 to penetrate the septum 24 of the medicament cartridge 19. The distal end of the needle 17 is sufficiently sharp to allow the needle to penetrate the patient's skin.

The attachment of the needle holder 18 with the medicament cartridge 19 may provide audible feedback, such as a clicking sound, informing the user that the needle has been inserted into the medicament cartridge 19.

Once the needle 17 has been inserted in to the medicament cartridge 19 and the needle holder 18 attached thereto, the device is ready to commence injection of the medicament. The distal end of the device 10 may then be placed against the injection site located on the patient's skin.

Figure 6:
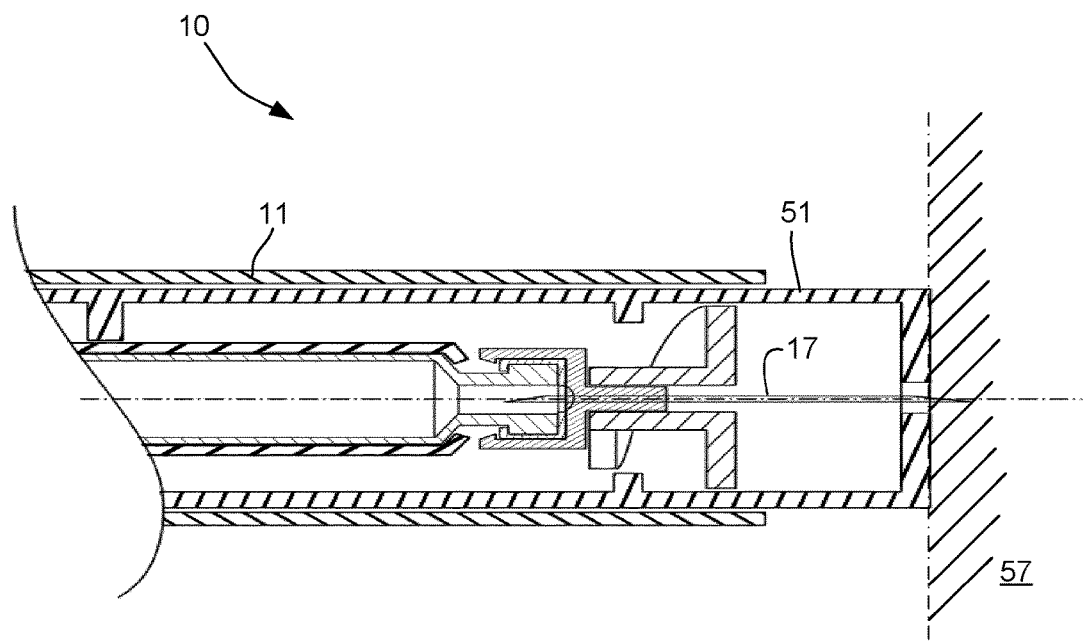
FIG. 6 is a side-on cross sectional schematic view of the device during an injection.

FIG. 6 shows a side-on cross-section of the auto-injector device 10 as the needle sleeve 51 moves, relative to the main body 11, in the proximal direction of the bold arrows beyond the predefined distance.

This relative movement can be caused by a user gripping the main body 11 and pushing the needle sleeve 51 towards the proximal end of the device 10. Alternatively, the distal end of the needle sleeve 51 may be held against the patient's skin at the injection site. As the user pushes the device 10 against the injection site, the outer wall of the main body 11 slides over needle sleeve 51, causing the needle sleeve 51 to retract relative to the main body 11.

Since the needle 17 and needle holder 18 are no longer coupled to the needle sleeve 51 and are instead fixed with respect to the medicament cartridge 19 and the main body 11, this further axial movement of the needle sleeve 51 causes the needle 17 to emerge from the aperture 25 in the distal end of the needle sleeve 51. If the device 10 has been placed against the injection site, the needle 17 pierces the patient's skin.

Once the needle holder 18 is fixed to the head of the medicament cartridge 19, the needle holder displacement element 52 cannot be displaced axially. Therefore, any subsequent proximal axial force applied to the needle sleeve 51, leads to a rotation of the needle sleeve pins 56 against the ramped surfaces 53 of the needle holder displacement element 52. The needle sleeve pins 56 become aligned with the grooves 54 located in the needle holder displacement element 52. The axial force applied to the needle sleeve 51 causes the needle sleeve pins 56 to pass through the grooves 54 located in the needle holder displacement element 52. The needle sleeve 51 thus disengages with the needle holder 18.

Further axial movement of the needle sleeve 51 with respect to the main body 11 leads to exposure of the needle 17 from the distal end of the needle sleeve, as shown in FIG. 6. The configuration shown in FIG. 6 illustrates when the device 10 is held against an injection site 57. The further axial movement of the needle sleeve 51 causes insertion of the needle 17 into the patient's skin.

While the embodiments described above refer to auto-injector devices, it should be borne in mind that other embodiments may be used in conjunction with other medicament delivery devices, for example syringes.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, $15^{th}$ edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codable amino acids, or amino acids, including non-codable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten. An example of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or a regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that can be useful include, for example, Fab fragments, F(ab')$_2$ fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof

The invention claimed is:
1. A medicament injection device comprising:
   a main body configured to receive a medicament cartridge,
   a needle sleeve axially movable with respect to the main body, a needle holder holding a needle, and a displacement element coupled to the needle holder and disengageably coupled to the needle sleeve;

wherein the needle sleeve and the displacement element are moveable in a proximal direction relative to the main body during use from a first position, in which the needle sleeve is coupled to the displacement element, to a second position, in which (i) the needle sleeve is uncoupled from the displacement element and (ii) the needle sleeve is moveable in the proximal direction relative to the displacement element; and wherein, upon axial displacement of the needle sleeve from the first position by a predefined distance in the proximal direction, the needle holder and the needle are displaced axially in the proximal direction.

2. The device of claim 1, wherein further axial movement in the proximal direction of the needle sleeve beyond the predefined distance causes the uncoupling of the needle sleeve from the displacement element.

3. The device of claim 1, wherein the displacement element comprises at least one ramped surface.

4. The device of claim 3, wherein the displacement element comprises at least one slot.

5. The device of claim 4, wherein the needle sleeve comprises at least one pin arranged to slide through the at least one slot when the displacement element and the needle sleeve are in rotational alignment.

6. The device of claim 5, wherein further axial movement of the needle sleeve causes a rotational movement of the at least one pin with respect to the at least one ramped surface so that the at least one pin aligns with the at least one slot, thereby causing the uncoupling of the needle sleeve from the displacement element.

7. The device of claim 5, wherein the at least one pin comprises two pins located circumferentially opposite from each other on an inner circumferential wall of the needle sleeve and the at least one slot comprises two respective slots for receiving the two pins located circumferentially opposite from each other.

8. The device of claim 1, containing the medicament cartridge, wherein the axial displacement of the needle holder and the needle in the proximal direction causes a proximal end of the needle to pierce a cartridge septum.

9. The device of claim 8, wherein the medicament cartridge comprises a male part and the needle holder comprises a female part and wherein the male part and the female part are configured to form a frictional fit subsequent to the axial displacement of the needle holder by the predefined distance.

10. The device of claim 9, wherein the needle holder further comprises a lip to prevent subsequent axial displacement of the needle holder and the needle with respect to the medicament cartridge subsequent to the axial displacement of the displacement element by the predefined distance.

11. The device of claim 1, wherein the device contains the medicament cartridge containing a medicament.

12. A method of operating a medicament injection device, the method comprising:

pushing a needle sleeve disengageably coupled to a displacement element in a proximal axial direction from a first position, in which the needle sleeve is coupled to the displacement element, to a second position, in which the needle sleeve is uncoupled from the displacement element, wherein pushing the needle sleeve causes proximal movement of a needle holder and a needle, wherein a proximal end of the needle is caused to pierce a penetrable barrier of a medicament cartridge.

13. The method of claim 12, wherein the needle sleeve is in direct contact with the displacement element when the needle sleeve is in the first position.

14. The method of claim 12, wherein pushing the needle sleeve in the proximal axial direction causes (i) the displacement element to rotate and (ii) the displacement element to move relative to a main body of the medicament injection device.

15. The method of claim 14, wherein pushing the needle sleeve in the proximal axial direction beyond a predefined distance causes the uncoupling of the needle sleeve from the displacement element by rotationally aligning the needle sleeve and the displacement element.

16. The method of claim 15, wherein pushing the needle sleeve in the proximal axial direction beyond the predefined distance causes at least one pin of the needle sleeve to slide through at least one slot of the displacement element to cause the uncoupling of the needle sleeve from the displacement element.

17. The method of claim 12, wherein pushing the needle sleeve in the proximal axial direction beyond a predefined distance causes at least one pin of the needle sleeve to slide through at least one slot of the displacement element.

18. A medicament injection device comprising:

a main body configured to receive a medicament cartridge, a needle sleeve axially movable with respect to the main body, a needle holder holding a needle, and a displacement element coupled to the needle holder and disengageably coupled to the needle sleeve, the displacement element comprising at least one ramped surface and at least one slot;

wherein the needle sleeve comprises at least one pin arranged to slide through the at least one slot when the displacement element and the needle sleeve are in rotational alignment, wherein, upon axial displacement of the needle sleeve by a predefined distance in a proximal direction, the needle holder and the needle are displaced axially in the proximal direction.

19. The device of claim 18, wherein further axial movement of the needle sleeve causes a rotational movement of the at least one pin with respect to the at least one ramped surface so that the at least one pin aligns with the at least one slot, thereby causing the disengagement of the needle sleeve from the displacement element.

20. The device of claim 18, wherein the at least one pin comprises two pins located circumferentially opposite from each other on an inner circumferential wall of the needle sleeve and the at least one slot comprises two respective slots for receiving the two pins located circumferentially opposite from each other.

* * * * *